United States Patent [19]

Krüger et al.

[11] 4,101,570

[45] Jul. 18, 1978

[54] PROCESS FOR THE PRODUCTION OF PERCARBOXYLIC ACID SOLUTIONS IN ORGANIC SOLVENTS

[75] Inventors: Manfred Krüger; Gerd Schreyer, both of Grossauheim; Otto Weiberg, Neu-Isenburg, all of Germany

[73] Assignee: Deutsche Gold- und Silber-Scheideanstalt Vormals Roessler, Frankfurt, Germany

[21] Appl. No.: 425,290

[22] Filed: Dec. 17, 1973

[30] Foreign Application Priority Data

Dec. 22, 1972 [DE]   Fed. Rep. of Germany ....... 2262970

[51] Int. Cl.$^2$ ............................................. C07C 179/10
[52] U.S. Cl. .............................................. 260/502 R
[58] Field of Search ............. 260/502 R, 502 A, 610 R

[56] References Cited

U.S. PATENT DOCUMENTS 3,180,886   12/1965   Silbert et al. ......................... 260/465

FOREIGN PATENT DOCUMENTS

| | | | |
|---|---|---|---|
| 221,813 | 7/1957 | Australia ........................ | 260/502 R |
| 2,312,281 | 9/1974 | Fed. Rep. of Germany. | |
| 2,141,156 | 3/1973 | Fed. Rep. of Germany ... | 260/502 R |
| 2,145,603 | 3/1973 | Fed. Rep. of Germany ... | 260/502 R |
| 1,165,576 | 3/1964 | Fed. Rep. of Germany ... | 260/502 R |
| 38-4,862 | 4/1963 | Japan .............................. | 260/502 R |
| 949,094 | 2/1964 | United Kingdom ............ | 260/502 R |

OTHER PUBLICATIONS

Silbert et al., "Reprint J. Org. Chemistry", vol. 27, p. 1336 (1962), pp. 1336–1342.

*Primary Examiner*—James O. Thomas, Jr.
*Assistant Examiner*—Werren B. Lone
*Attorney, Agent, or Firm*—Cushman, Darby & Cushman

[57] ABSTRACT

There is provided a continuous process for the production of water free or substantially water free peralkanoic acids with 2 to 4 carbon atoms by reaction of aqueous hydrogen peroxide with an alkanoic acid having 2 to 4 carbon atoms in the presence of acidic catalyst at a mole ratio of hydrogen peroxide to alkanoic acid of 0.5 to 30:1, preferably from 0.8 to 20:1, in a reactor by countercurrent extraction of the reaction solution with an organic solvent, recovery of a substantially water free solution of peralkanoic acid as extract and in a given case, eventually after addition of an additional solvent, dehydration of the extract by azeotropic distillation, the entire aqueous raffinate or a portion thereof is led to an evaporator unit, in which the water brought in with the starting materials and formed during the reaction is distilled off under reduced pressure, whereupon the concentrated raffinate as well as in a given case the non-concentrated portion of the raffinate is returned to the reactor and the reactor is replenished with sufficient aqueous hydrogen peroxide and alkanoic acid that the starting conditions are again produced.

18 Claims, 1 Drawing Figure

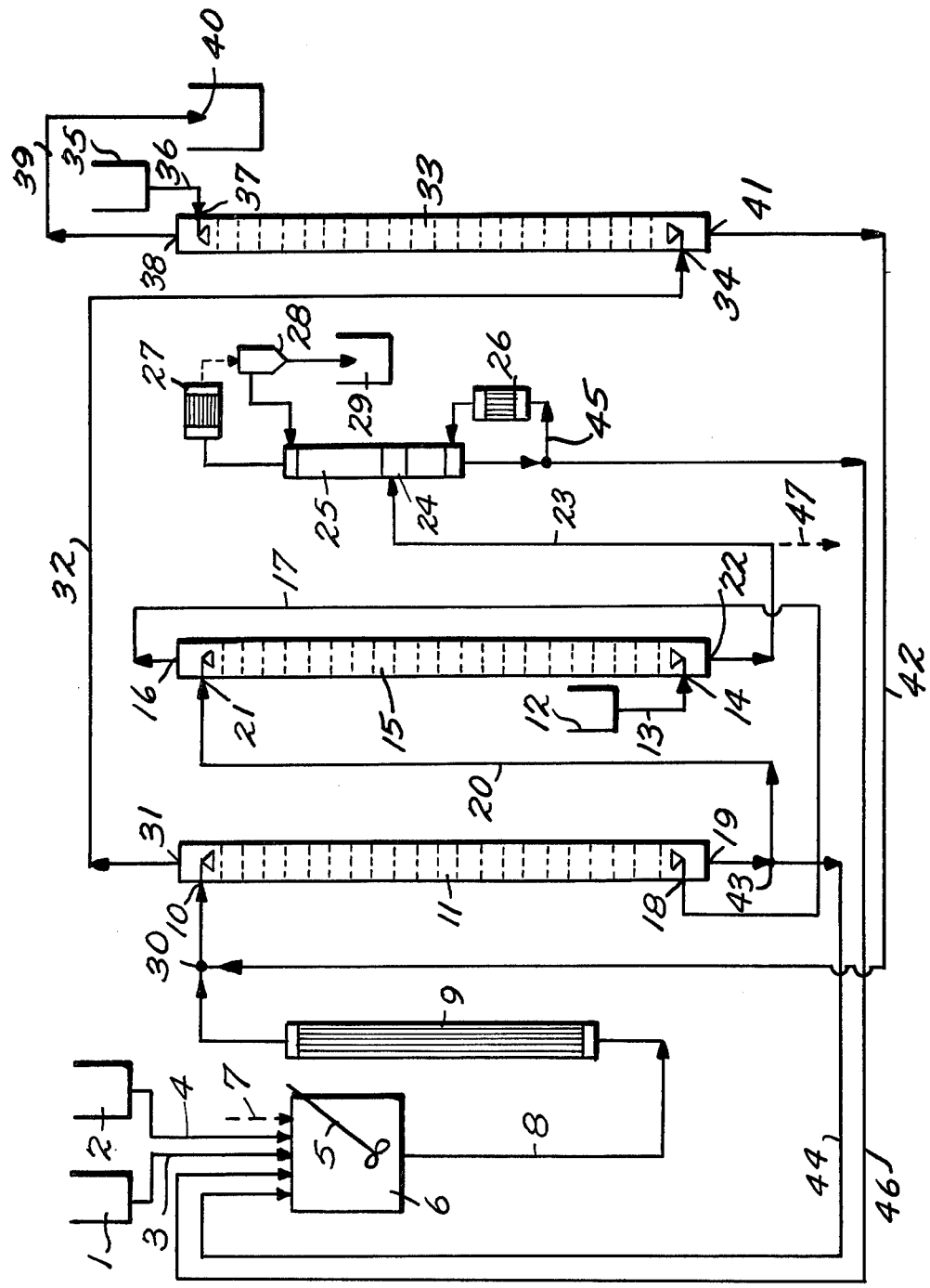

PROCESS FOR THE PRODUCTION OF PERCARBOXYLIC ACID SOLUTIONS IN ORGANIC SOLVENTS

Percarboxylic acids have received growing significance as reagents for converting alpha olefins to alpha epoxides and for converting cyclic ketones to lactones. The easily accessible aqueous percarboxylic acid solutions, for example according to Weiberg German Pat. Nos. 1.165,576, 1,170,926 and U.S. Pat. No. 3,264,346 are not so desirable for these reactions due to the presence of water.

Water free or substantially water free solutions of percarboxylic acids in organic solvents can be produced in various ways, for example, by extraction or by azeotropic separation of water from aqueous percarboxylic acid solutions with an excess of organic solvent. Both processes are expensive in energy because in each case in the production of the aqueous percarboxylic acid solution water and additionally the percarboxylic acid must be distilled and in the latter case this water again must be separated by azeotropic distillation (see Ullmann, Enzyclopadie d. Techn. Chemie, Erganzungsband (1970), New Processes, page 181 et seq. and Swern, Organic Peroxides Vol. 1 (1970) page 313 et seq.).

It is known that organic percarboxylic acid solutions can be obtained by the extraction of the percarboxylic acid from a mixture previously brought into equilibrium of the acid catalyzed reaction: carboxylic acid + hydrogen peroxide ⇌ percarboxylic acid + water with a water immiscible solvent. As acid catalysts for regulating the equilibrium there can be employed mineral acids (as, for example, sulfuric acid or phosphoric acid), inorganic, especially acid salts (as, for example sodium hydrogen sulfate, compare D. Swern, Chem. Rev. Vol. 45 pages 1–68 (1949)), as well as acid ion exchangers (Kurhajec U.S. Pat. No. 3,140,312).

Thereby the extraction for recovery of water free percarboxylic acid solutions is carried out either in several steps (see German Auslegeschrift No. 1,048,569) or in a single step (see German Offenlegungsschrift No. 1,618,625). In each case the raffinate was rejected. However, this raffinate still contains in part considerable amounts of hydrogen peroxide which are thereby lost.

The object of the present invention is to develop an industrial, continuous process for the production of water free or substantially water free solutions of percarboxylic acids, especially peralkanoic acids of 2 to 4 carbon atoms such as peracetic acid, perpropionic acid, perbutyric acid, perisobutyric acid, by extraction with incorporation of the rejected raffinate.

It has now been found that the raffinate which results in the countercurrent extraction of an equilibrium solution of hydrogen peroxide and a carboxylic acid with 2 to 4 carbon atoms, e.g., acetic acid, propionic acid, butyric acid or isobutyric acid, (initial mole ratio 0.5 to 30:1, preferably 0.8 to 20:1) percarboxylic acid, acid catalyst, e.g., sulfuric acid or phosphoric acid or any of the other acid catalysts set forth above, and water with organic solvent and still contains hydrogen peroxide can be concomitantly used after separation from the substantially water free extract of the percarboxylic acid, if the entire aqueous raffinate or a portion thereof is led to an evaporator unit in which the water brought in with the starting materials and also that formed during the reaction is distilled off under reduced pressure, whereupon the concentrated raffinate as well as the, in a given case, non-concentrated portion of the reactor is returned to the reactor and the reactor is replenished with sufficient aqueous hydrogen peroxide and carboxylic acid that the starting conditions are again produced.

The reduced pressure is not critical and can be for example from 20 to 200 Torr.

It is not necessary to distill off the above defined amount of water from the entire raffinate. It can even be more favorable to remove this amount of water only a part of the raffinate and to again return the thus concentrated portion of the raffinated together with the untreated raffinate to the reactor.

From the percarboxylic acid containing extract obtained, which can be recovered by extraction with hydrocarbons, e.g., aromatic hydrocarbons such as benzene, toluene, xylene, chlorinated hydrocarbons, e.g., 1,2-dichloroethane, chloroform, carbon tetrachloride, 1,2-dichloropropane, 1,3-dichloropropane, 1,1-dichloroethane, chlorobenzene, benzyl chloride there can be substantially recovered the concomitantly extracted small amounts of hydrogen peroxide by a continuous subsequent extraction with water or an aqueous solution of the acid catalyst. The thus resulting aqueous solution of hydrogen peroxide is then again returned to the reaction mixture.

FIG. 1 of the drawings illustrates the process of the invention in which the extraction of the percarboxylic acid takes place in two steps and in which the peralkanoic acid extract specifically is lighter than the aqueous raffinate.

According to the drawings as soon as the apparatus system is filled, only a portion of the aqueous raffinate substantially free of percarboxylic acid and carboxylic acid is passed from the first extraction column 11 via line 20 into the second extraction column 15 at 21. Another, generally larger, part of this raffinate, e.g., 75% by volume, is branched off at 43 and returned over the line 44 into the mixing vessel 6. Simultaneously there is withdrawn as much raffinate from the bottom of the distillation column 25 via branch line 45 to the evaporator unit 26 as corresponds to the difference between the amounts introduced to the distillation column 25 at point 24 from bottom 22 of column 15 via line 23 and withdrawn from the separator at 29. Raffinate is likewise returned to the mixing vessel 6 over line 46. The mixture in vessel 6 is stirred by stirrer 5 and is enriched with aqueous hydrogen peroxide coming from the vessel 1 via line 3 and carboxylic acid (with or without water) coming from vessel 2 via line 4 in such amounts that after establishment of equilibrium in reactor 9 the original concentration of the components is maintained. Initially sulfuric acid is added via line 7 to mixing vessel 6. The mixture is passed via line 8 to reactor 9.

An amount of water is separated off in the distillation column 25 and then condensed in condenser 27 and separated from other volatiles in separator 28 which corresponds to the total of (1) that brought in with the aqueous hydrogen peroxide, (2) that which is formed by reaction and (3) the amount of water entrained in the reextraction in the third extraction column 33. Water coming from storage vessel 35 via line 36 is added to column 33 at point 37. Percarboxylic acid in the organic solvent is withdrawn via line 39 and recovered in vessel 40.

It is advantageous to exchange the aqueous cycling solution from time to time, preferably continuously, in order to hold the content of entrained impurities to such a level that the decomposition of the active oxygen compounds remains low. Thus intermittently cycling solution can be withdrawn via line 47.

Instead of the above mentioned extraction column, there can also be used other extraction apparatuses as, for example, Podbielniak extractors. Thin layer evaporators are also suitable as evaporators.

Benzene or other extracting liquid is supplied from storage tank 12 via line 13 to extraction column 15 at 14.

Extracted material from top 16 of column 15 goes via line 17 to the first extraction column 11 where it is introduced at 11. Extracted material from the top 16 of column 11 goes via line 32 to the third extraction column 33 where it is introduced at 34. Raffinate from the bottom 41 of column 33 goes via line 42 to junction 30 where it is combined with the reaction mixture from reactor 9 and enters column 11 at 10.

As already stated the raffinate can be returned either completely or only partially to the evaporator unit. If the extraction is carried out in two steps the ratio in which the raffinate is distributed from the first extraction between the second extraction column 15 and the mixing vessel 6 at the branching point 43 is dependent upon the extraction constants of the percarboxylic acid and the carboxylic acid in the extraction system used and on the economical separation of the required amount of water. In carrying out the extraction in one step only the the economical separation of water is significant for the distribution ratio; i.e., column 15 is eliminated. Generally the ratio of the part of the raffinate which returns directly to the reactor to the part which is led over a second extraction of the evaporator unit should be in the volume ratio 10:1 to 1:5, preferably in the ratio 6:1 to 1:1.

The process for working up the raffinate according to the process of the invention can be inserted in all known processes for the recovery of organic percarboxylic acid solutions which include an extraction of the aqueous equilibrium mixture. The process is especially useful in the recovery of peralkanoic acids having 2 to 4 carbon atoms.

There can be employed any conventional aqueous hydrogen peroxide solution, e.g., a 30 to 90% solution by weight, usually not over 70% by weight hydrogen peroxide.

EXAMPLE 1

In an apparatus consisting of glass and stainless steel as is shown in the drawings and as described above there were brought in by way of the mixing vessel 6 all together 6.5 liters of a mixture of 35% aqueous hydrogen peroxide and propionic acid in the addition molar ratio hydrogen peroxide:propionic acid = 4:1 with the addition of 30 weight % of sulfuric acid based on the sum of the aqueous hydrogen peroxide and propionic acid. The solution passes to the reactor 9, a glass double jacketed tube having a content of 335 ml. filled with glass Raschig rings and heated to 55° C., with an average residence time of 10 minutes and is then again cooled to room temperature, was led to the top a first pulsating perforated plate extraction column 11 having a diameter of 50 mm. with 60 perforated plates. The raffinate of this column was introduced ¼ the way up a second pulsating perforated plate extraction column 15 having a diameter of 50 mm. with 50 perforated plates and extracted there with fresh benzene; the entire extract of the second extraction column was led to the bottom of the first extraction column. In a circulation evaporator having a capacity of 270 ml with a 30 cm column having a 30 mm diameter erected thereon and filled with 3mm. glass spirals there was distilled off the reaction water from the raffinate of the extraction column 15 at about 40 Torr, 56° C. sump temperature, 34° C. head temperature and a reflux ratio of 1:2 to 1:8. The bottom product of the distillation cooled to room temperature and ¾ of the raffinate of the first extraction column were returned into the mixing vessel 6.

From this time on, the addition of reaction mixture was stopped and henceforth there were only added to the mixing vessel 6 128 ml/h of 50% aqueous hydrogen peroxide and 272 ml/h of propionic acid with the addition of 20 mg/h of dipicolinic acid as a stabilizer. The mixture obtained there was pumped at the rate of 2 liters/h through the reaction vessel and cooler and after that had the following composition in the stationary state with regard to the essential components:

18.7 weight % hydrogen peroxide; 9.2 weight % perpropionic acid; 4.6 weight % propionic acid; 23.1 weight % sulfuric acid; 44.4 weight % water. Eventually developed gas through decomposition of the peroxygen compounds was let out of the apparatus above the cooler. There were used 1750 ml/h of benzene for the extraction.

The raffinate of the column 15 had the average following composition:

21.6 weight % hydrogen peroxide; 51.5 weight % water and 29.6 weight % sulfuric acid as well as traces of perpropionic acid. In the evaporator there were distilled off 115 ml/h of water. The mixture coming out of the bottom had the following average composition:

27.6 weight % hydrogen peroxide; 33.9 weight % sulfuric acid and 38.5 weight % water and was returned into the mixing vessel 6.

The benzene extract taken away from the first extraction column (about 2000 ml/h) contained in the stationary state 9.8 weight % perpropionic acid; 7.8 weight % propionic acid; 0.4 weight % water; 0.2 weight % hydrogen peroxide and less than 0.0015 weight % sulfuric acid. The apparatus was operated in this manner for 824 hours. The yield of perpropionic acid in the benzene extract amounted to 87.0% based on the hydrogen peroxide fed in.

The perpropionic acid extract recovered in Example 1 (about 2000 ml/h) having about 0.4 weight % water and 0.2 weight % hydrogen peroxide was subsequently extracted in an additional pulsating perforated plate extraction column 33 with 20 ml/h of water to which 0.1 gram/l of sodium pyrophosphate was added to stabilize the hydrogen peroxide to be extracted; the aqueous percarboxylic acid, carboxylic acid and hydrogen peroxide containing extract was again returned to the reaction mixture before the first extraction and instead of 115 ml/h there was now distilled off 130 ml/h of water in the evaporator unit to equalize the water balance. The departing bottom mixture corresponded to the above mentioned bottom mixture. The withdrawn benzene extract contained after the hydrogen peroxide-reextraction 9.8 weight % perpropionic acid; 7.8 weight % propionic acid; 1.0 weight % water and 0.04 weight % hydrogen peroxide. The yield of perpropionic acid increased about 3.5% to 90.5% based on the hydrogen peroxide fed in.

In the same manner as Example 1 but using instead 20 ml/h of water with 20 ml/h of 25% aqueous sulfuric acid for the subsequent extraction, there was obtained a benzene extract having about 9.8 weight % perpropionic acid; 7.8 weight % propionic acid; 0.5 weight % water and 0.05 weight % hydrogen peroxide.

EXAMPLE 2

In a manner analogous to the described production of a nearly water free benzene solution of perpropionic acid in Example 1 the apparatus was operated to produce a nearly water free, benzene solution of perisobutyric acid by extraction of an equilibrium mixture of 50 weight %, aqueous hydrogen peroxide and isobutyric acid in the addition molar ratio of hydrogen peroxide; isobutyric acid = 20:1, with addition of 20 weight % sulfuric acid based on the sum of aqueous hydrogen peroxide and isobutyric acid. Hereby the reactor 9 had a volume of 750 ml and division of the raffinate of the first extraction column was so taken that 1/5 was led to the second extraction column and 4/5 unchanged was returned again to the mixing vessel 6.

In the stationary condition, there were fed into the mixing vessel 6 heated to 35° C. 110 ml/h of 50% aqueous peroxide and 180 ml/h of isobutyric acid with the addition of 15 mg/h of dipicolinic acid as a stabilizer. The mixture obtained there was pumped at the rate of 3.5 l/h through the reaction vessel (average residence time 13 minutes) and cooler and had in regard to the essential components the following average composition: 37.5 weight % hydrogen peroxide; 0.8 weight % isobutyric acid; 5.0 weight % perisobutyric acid; 16.7 weight % sulfuric acid and 40.0 weight % water. There was used 435 ml/h of benzene for the extraction.

The raffinate of the column 15 had the following average composition: 39.8 weight % hydrogen peroxide; 42.5 weight % water; and 17.6 weight % sulfuric acid.

In the evaporator there were distilled off 100 ml/h of water (together with only 0.2 weight % hydrogen peroxide and 0.5 weight % of perisobutyric acid). The mixture leaving the bottom contained: 46.2 weight % hydrogen peroxide; 20.6 weight % sulfuric acid; and 33.2 weight % water. The benzene extract withdrawn from the first extraction column 11 was subsequently extracted in the third extraction column 33 with 20 ml/h of water to which 0.1 g/l of sodium pyrophosphate was added for stabilization of the hydrogen peroxide. The benzene extract withdrawn (615 ml/h) after the hydrogen peroxide extraction contained 26 weight % perisobutyric acid; 8 weight % isobutyric acid; 2 weight % water and 0.3 weight % hydrogen peroxide. The apparatus was operated in this manner for 376 hours.

EXAMPLE 3

In an apparatus corresponding to that in the drawings in which the first extraction consisted of five successive mixer settlers each having a capacity of 250 ml and in which both additional extraction steps were mixing there was carried out an operation for the product of an almost water free benzene solution of perpropionic acid by extraction of an equilibrium mixture of 50 weight % aqueous hydrogen peroxide and propionic acid in the addition molar ratio hydrogen peroxide:propionic acid = 10:1 with addition of 50 weight % sodium hydrogen sulfate based on the total of the aqueous hydrogen peroxide and propionic acid. Hereby the reactor 9 had a volume of 250 ml. In the stationary condition there was withdrawn 45 ml/h of 50% aqueous hydrogen peroxide and 75 ml/h of propionic acid with addition of 6 mg/h of dipicolinic acid as a stabilizer together with the material from the bottom of the evaporator unit into which the entire raffinate of the last mixer settler extraction stage was flowed, and the solution fed into the mixing vessel 6. The mixture obtained there was pumped at the rate of 1.0 l/h through the reaction vessel heated to 55° C. (average residence time about 15 minutes) and through the cooler and had after than in regard to the essential components the following average composition: 28.6 weight % hydrogen peroxide; 1.55 weight propionic acid; 5.7 weight % perpropionic acid; 34.2 weight % sodium hydrogen sulfate; balance water. For the extraction there were used 210 ml/h of benzene. In the evaporator there were distilled off 40 ml/h of water (together with only 0.2 weight % hydrogen peroxide and 1.0 weight % perpropionic acid). The benzene extract withdrawn (300 ml/h) contained in the stationary condition 21.7 weight % perpropionic acid; 9.2 weight % propionic acid; 1.5 weight % water and 0.8 weight % hydrogen peroxide; the NaHSO$_4$ content was below 0.2 weight %.

What is claimed is:

1. In a continuous process for the production of substantially water free peralkanoic acid having 2 to 4 carbon atoms, said process comprising reacting in a reactor aqueous hydrogen peroxide with an alkanoic acid having 2 to 4 carbon atoms in the presence of an acidic catalyst at an addition mole ratio of hydrogen peroxide to alkanoic acid of 0.5 to 30:1 to form peralkanoic acid and water, counter-currently extracting the aqueous reaction solution with a water immiscible organic solvent, recovering a substantially water free solution of peralkanoic acid in said solvent, and dehydrating the extract by azeotropic distillation the improvement comprising taking at least a portion of the hydrogen peroxide containing aqueous raffinate from said extraction, and feeding it to an evaporating unit, distilling off at least a portion of the water from said raffinate under reduced pressure to form a hydrogen peroxide containing concentrated raffinate and returning the concentrated raffinate to the reactor together with sufficient fresh aqueous hydrogen peroxide and alkanoic acid to restore the starting conditions.

2. A process according to claim 1 wherein the pressure in the evaporating unit is 20 to 200 Torr.

3. A process according to claim 1 wherein the solvent is a chlorinated hydrocarbon or an aromatic hydrocarbon.

4. A process according to claim 3 wherein the alkanoic acid employed has 3 to 4 carbon atoms.

5. A process according to claim 4, wherein the alkanoic acid is propionic acid or isobutyric acid.

6. A process according to claim 1, wherein the solvent is a chlorinated hydrocarbon or a hydrocarbon.

7. A process according to claim 6 wherein the solvent is an aromatic hydrocarbon.

8. A process according to claim 7, wherein the solvent is benzene.

9. A process according to claim 3, wherein the solvent boils below water.

10. A process according to claim 3, wherein the mole ratio of hydrogen peroxide to alkanoic acid is 0.8 to 20:1.

11. A process according to claim 3, wherein all of the raffinate is fed to the evaporator.

12. A process according to claim 3 wherein only a portion of the raffinate is fed to the evaporator.

13. A process according to claim 12, wherein there is also returned to the reactor the non-concentrated raffinate.

14. A process according to claim 3 wherein the extraction is carried out in two steps and wherein the incompletely extracted aqueous raffinate from the first extraction is divided into two parts, one of said parts is returned to the reactor and the other part is exhaustively extracted with an aromatic hydrocarbon or chlorinated hydrocarbon and the total organic extract of the second extraction is returned to the first extraction unit and only the aqueous raffinate of the second extraction is led to the evaporator unit.

15. A process according to claim 12 wherein the part of the raffinate which is returned directly to the reactor to the part fed to the evaporator unit has the volume ratio of 10:1 to 1:5.

16. A process according to claim 15 wherein the volume ratio of the raffinate returned directly to the reactor to the raffinate fed to the evaporator unit is from 6:1 to 1:1.

17. A process according to claim 3 wherein the pressure in the evaporating unit is 20 to 200 Torr.

18. A process according to claim 17 wherein the solvent is selected from the group consisting of benzene, toluene, xylene, 1,2-dichloroethane, chloroform, carbon tetrachloride, 1,2-dichloropropane, 1,3-dichloropropane, 1,1-dichloroethane, chlorobenzene, and benzyl chloride.

* * * * *